(12) United States Patent
Bohner

(10) Patent No.: US 6,642,285 B1
(45) Date of Patent: Nov. 4, 2003

(54) IMPLANT COMPRISING CALCIUM CEMENT AND HYDROPHOBIC LIQUID

(75) Inventor: Marc Bohner, Aarau (CH)

(73) Assignees: Robert Mathys Stiftung, Bettlach (CH); Stratec Medical AG, Oberdorf (CH)

(*) Notice: Subject to any disclaimer, the term of this patent is extended or adjusted under 35 U.S.C. 154(b) by 0 days.

(21) Appl. No.: 09/889,655

(22) PCT Filed: Jan. 2, 1999

(86) PCT No.: PCT/EP99/00684
§ 371 (c)(1),
(2), (4) Date: Jul. 19, 2001

(87) PCT Pub. No.: WO00/45867
PCT Pub. Date: Aug. 10, 2000

(51) Int. Cl.$^7$ .............................. A61K 6/08; A61F 2/02; C08K 5/51
(52) U.S. Cl. ........................ 523/115; 523/113; 523/116; 524/127; 524/801; 524/803; 424/425; 424/501; 424/502
(58) Field of Search ................................. 523/115, 116, 523/125, 113; 424/501, 502, 425; 524/801, 803, 127

(56) References Cited

U.S. PATENT DOCUMENTS

| | | | |
|---|---|---|---|
| 3,552,357 A | * | 1/1971 | Quayle et al. |
| 3,907,692 A | * | 9/1975 | Ullmann et al. |
| 4,322,398 A | | 3/1982 | Reiner et al. |
| 4,439,420 A | * | 3/1984 | Mattei et al. ................. 424/78 |
| 4,596,574 A | * | 6/1986 | Urist |
| 4,959,104 A | | 9/1990 | Iino et al. |
| 5,055,307 A | * | 10/1991 | Tsuru et al. |
| 5,063,257 A | * | 11/1991 | Akahane et al. |
| 5,152,836 A | * | 10/1992 | Hirano et al. ............... 106/690 |
| 5,648,097 A | * | 7/1997 | Nuwayser |
| 5,681,873 A | | 10/1997 | Norton et al. |
| 5,866,155 A | * | 2/1999 | Laurencin .................. 424/425 |
| 6,153,644 A | * | 11/2000 | Owens et al. |

FOREIGN PATENT DOCUMENTS

| | | | | |
|---|---|---|---|---|
| EP | 538 913 A1 | * | 4/1993 | ........... A61L/27/00 |
| JP | 5-85914 | | 9/1988 | |

OTHER PUBLICATIONS

XP002116821, Database WPI, Derwent Publications Ltd., London, GB; AN 1988–311471, JP 63 229058 A (Oshima Y), Sep. 22, 1988, abstract.
XP002116822, Database WPI, Derwent Publications Ltd., London, GB; AN 1990–280098, JP 02 198560 A (NGK Spark Plug Co Ltd), Aug. 7, 1990, abstract.
XP002116823, Database WPI, Derwent Publications Ltd., London, GB; AN 1989–359830, JP 01 268560 A (Advance KK), Oct. 26, 1989, abstract.
Patent Abstracts of Japan, Publication No.: 01111762, Publication Date: Apr. 28, 1989, Tokuyama Soda Co Ltd, Title: Hardening Composition.
Patent Abstracts of Japan, Publication No. 01139516, Publication Date: Jun. 1, 1989, Tokuyama Soda Co Ltd; Title: One Paste–Type Restorative Material.

* cited by examiner

*Primary Examiner*—Tae H. Yoon
(74) *Attorney, Agent, or Firm*—Rankin, Hill, Porter & Clark LLP

(57) ABSTRACT

A composition including a hydraulic cement for implantation in a human or animal body. The hydraulic cement includes a first component, a second component, and a third component. The first component includes a calcium source while the second component includes water. The third component is a hydrophobic liquid. The composition hardens after mixing of the components, and results in a cement with open macroporosity enabling a rapid bone ingrowth.

62 Claims, No Drawings

IMPLANT COMPRISING CALCIUM CEMENT AND HYDROPHOBIC LIQUID

This application is a 371 of PCT/EP99/00684 filed on Feb. 2, 1999.

This invention concerns a composition in accordance with the pre-characterising portion of claim 1 and a method for producing hardened calcium-containing cement particles or a porous calcium-containing matrix for use in the human or animal body according to the pre-characterising portion of claim 47.

The porous calcium-containing matrix block or round calcium-containing particles are obtained by combining a calcium-containing hydraulic cement paste with a hydrophobic solution such that (i) the calcium-containing hydraulic cement paste is obtained by mixing one or several powders with an aqueous lubricant; (ii) the lubricant comprises water; (iii) the calcium-containing cement paste hardens with time; (iv) the hydrophobic solution hardly dissolves or do not dissolve in the calcium-containing paste and vice versa; (v) the calcium-containing cement paste and the hydrophobic solution are mixed together to form a so-called emulsion. Depending on the composition of the emulsion, the emulsion is made out of particles of the calcium-containing paste in the hydrophobic solution or out of particles of the hydrophobic solution in the calcium-containing paste; (vi) The mixing of the emulsion is stopped at a given time to obtain either calcium-containing particles floating in the hydrophobic solution or a calcium-containing matrix having pores filled with the hydrophobic solution.

Calcium phosphates are known to be biocompatible and in most cases osteoconductive. They represent therefore a good alternative to bone grafting. Different forms have been given to calcium phosphates. In most cases, calcium phosphate are sold as granules of about 0.5 to 2.0 mm diameter. Just before implantation, the granules are mixed with the blood of the patient and applied to the desired place. The advantage of this technique is its simplicity and the fact that bone can easily grow in between the granules. However, the granules do not hold together and can migrate away from the defect. For example in the dental area, ceramic granules can migrate out from the gingiva into the mouth which is for obvious reasons not desirable. Furthermore, most commercial granules cannot be easily packed in large amounts in a given defect, because they are not round. Calcium phosphates are also sold as block. On the contrary to granules, blocks can have rather large mechanical properties, but they cannot be shaped according to the bone defect. Furthermore, it is difficult to fabricate a block that has an open-porous structure enabling a rapid bone ingrowth, and when it is the case, the block has low mechanical properties. Another alternative to sell calcium phosphates is as cements. The cements are made of a mixture of one or several calcium phosphate powders and one aqueous solution. Upon mixture with the aqueous solution, the calcium phosphate powders dissolve and precipitate into another calcium phosphate. Through this precipitation, the paste hardens forming a fine and homogeneous nanoporous or microporous matrix. Such so-called calcium phosphate cements are moldable and injectable, and can have rather large mechanical properties (e.g. more than 100 MPa in compressive strength). However, these cements do not have an open macropprosity enabling a rapid bone ingrowth. In this patent, we are presenting a method and compositions that respond to the problems described above, i.e. enable the obtention of, among others a highly-resistant open-macroporous matrix;

an injectable open-macroporous matrix; or round calcium phosphate particles.

The present invention as claimed aims at solving the above described problems. The present invention provides a cement as defined in claim 1 and a method for producing hardened calcium-containing cement particles or a porous calcium-containing matrix for use in the human or animal body as defined in claim 47.

The various features of novelty that characterize the invention are pointed out with particularity in the claims annexed to and forming part of this disclosure. For the better understanding of the invention, its operating advantages and specific objects attained by its use, reference should be made to the accompanying examples in which preferred embodiments of the invention are illustrated in detail.

Further in this description, the use of calcium phosphate hydraulic cement paste will be described. However, calcium sulphate hydraulic cement (gypsum) can also be used and should be therefore included in the calcium phosphate hydraulic cement.

The principle of this invention is to mix a calcium phosphate hydraulic cement paste with a hydrophobic liquid. If the composition of the cement and the hydrophobic liquid are well-chosen, an emulsion is obtained. It can be an emulsion of the cement paste in the hydrophobic liquid or of the hydrophobic liquid in the calcium phosphate paste. If the cement paste hardens in a optimized way, the emulsion can be frozen in its actual structure leading to either a hydrophobic liquid entrapped in a calcium phosphate matrix or calcium phosphate particles or structure floating in a hydrophobic liquid. In the case of a hydrophobic liquid entrapped in a calcium phosphate matrix, the shape, the volume and the interconnectivity of the pores filled with the hydrophobic liquid can be varied depending on the composition of the initial mixture. The possibilities are described herein.

Preferably the hydrophobic liquid is selected from the group of:

ricinoleic acid ($C_{17}H_{33}OCOOH$), linoleic acid ($C_{17}H_{31}COOH$), palmitic acid ($C_{15}H_{31}COOH$), palmitoleic acid ($C_{15}H_{29}COOH$), stearic acid ($C_{17}H_{35}COOH$), linolenic acid ($C_{17}H_{29}COOH$), arachidic acid ($C_{19}H_{39}COOH$), myristic acid ($C_{13}H_{27}COOH$), lauric acid ($C_{11}H_{23}COOH$), capric acid ($C_9H_{19}COOH$), caproic acid ($C_5H_{11}COOH$), oleic acid ($C_{17}H_{33}COOH$), caprylic acid ($C_7H_{15}COOH$), erucic acid ($C_{21}H_{41}COOH$), butyric acid ($C_3H_7COOH$), ethyl myristate ($C_{13}H_{27}COOC_2H_5$), ethyl oleate ($C_{17}H_{33}COOC_2H_5$), ethyl palmitate ($C_{15}H_{31}COOC_2H_5$), ethyl linoleate ($C_{17}H_{31}COOC_2H_5$), ethyl laurate ($C_{11}H_{23}COOC_2H_5$), ethyl linolenate ($C_{17}H_{29}COOC_2H_5$), ethyl stearate ($C_{17}H_{35}COOC_2H_5$), ethyl arachidate ($C_{19}H_{39}COOC_2H_5$), ethyl caprilate ($C_7H_{15}COOC_2H_5$), ethyl caprate ($C_9H_{19}COOC_2H_5$), ethyl caproate ($C_5H_{11}COOC_2H_5$), ethyl butyrate ($C_3H_7COOC_2H_5$), triacetin ($C_9H_{14}O_6$), alpha tocopherol ($C_{29}H_{50}O_2$), beta tocopherol ($C_{28}H_{48}O_2$), delta tocopherol ($C_{27}H_{46}O_2$), gamma tocopherol ($C_{28}H_{48}O_2$), benzyl alcohol ($C_7H_8O$), benzyl benzoate ($C_{14}H_{12}O_2$), methylphenol ($C_7H_8O$), di-n-butyl sebacate ($C_{18}H_{34}O_4$), diethylphthalate ($C_{12}H_{14}O_4$), glyceryl monooleate ($C_{21}H_{40}O_4$), lecithin [CAS registry number 8002-43-5], medium chain triglycerides, mineral oil [CAS registry number 8012-95-1], petrolatum [CAS registry number 8009-03-8], and liquid paraffines.

The vegetal oil—as a hydrophobic liquid—is a preferably selected from the group of:

canula oil [no CAS registry number], corn oil [CAS registry number 8001-30-7], cottonseed oil [CAS registry number 8001-29-4], peanut oil [CAS registry number 8002-03-7], sesame oil [CAS registry number 8008-74-0], castor oil [CAS registry number 8001-79-4], and soybean oil [CAS registry number 8001-22-7].

The first component comprises preferably:

calcium sulphate hemihydrate [$CaSO_4 \cdot \frac{1}{2}H_2O$], calcium pyrophosphate [$Ca_2P_2O_7$], calcium carbonate [$CaCO_3$], monocalcium phosphate monohydrate [$Ca(H_2PO_4)_2 \cdot H_2O$], monocalcium phosphate [$Ca(H_2PO_4)_2$], anhydrous dicalcium phosphate [$CaHPO_4$], dicalcium phosphate dihydrate [$CaHPO_4 \cdot 2H_2O$], octocalcium phosphate [$Ca_8H_2(PO_4)_6 \cdot 5H_2O$], alpha-tricalcium phosphate [alpha-$Ca_3(PO_4)_2$], beta-tricalcium phosphate [beta-$Ca_3(PO_4)_2$], hydroxyapatite [$Ca_5(PO_4)_3OH$], tetracalcium phosphate [$Ca_4(PO_4)_2O$], calcium-deficient hydroxyapatite [$Ca_{10-x}(HPO_4)_x(PO_4)_{6-x}(OH)_{2-x}$], fluoroapatite [$Ca_5(PO_4)_3F$], amorphous calcium phosphate, oxyapatite [$Ca_{10}(PO_4)_6O$], calcium oxide and calcium hydroxide [$Ca(OH)_2$] or a mixture of some or all of them.

The second component preferably further comprises sulphuric acid [$H_2SO_4$], phosphoric acid [$H_3PO_4$], citric acid or a mixture of them.

All mixtures and compositions of calcium phosphate cement are possible. Cements with a fast setting time and low initial viscosity are particularly well adapted. Most apatitic cements are more a problem because the hardening reaction may take place very slowly. In the latter case, the hydrophobic liquid has time to coalesce, preventing the obtention of an interconnected porous body. The end product of the cement reaction can vary from dicalcium phosphate dihydrate (Ca/P=1.0) to calcium deficient hydroxyapatite (Ca/P=1.33 to 1.67), octocalcium phosphate (Ca/P=1.33), poorly-crystallized hydroxyapatite (Ca/P=1.67) or poorly-crystallized carbonato-apatite (Ca/P=1.7). The cristallinity of the latter phases can vary over a broad range, i.e. from an amorphous phase to a highly-crystalline phase. After sintering (normally above 800° C.), the end product becomes calcuim pyrophosphate, alpha- or beta-TCP, well-crystallized hydroxyapatite, well-crystallized carbonatoapatite, tetracalcium phosphate [Ca/P=2.0, $Ca_4(PO_4)_2O$] or a mixture of some or all of them.

The particle size distribution and the agglomeration state of the calcium-containing powders determines the setting time of the cement, the volume of the cement mixing liquid needed to obtain a kneadable paste, and the rheological properties of the cement. As a following, the geometrical properties of the starting powders have an important effect on the properties of the final block. In principle, the powders should be non-agglomerated or non-aggregated, round, monodisperse, and small (around 1 micrometer in diameter). The presence of agglomerates or non-spherical particles increases the volume of aqueous solution required to knead the paste, hence increasing the final cement microporosity. The use of a monodisperse powder eases and accelerates the sintering step. The geometrical properties of the powder and in particular the particle size determine the amount of liquid which must be added to the powder to obtain a plastic or a liquid paste. If the particle size is too large, there is no domain where the mixture powder/aqueous solution is plastic. As a following, there is no possibility to vary the viscosity of the cement paste it is either powdery or liquid. Moreover, the particles tend to sediment in the liquid which is detrimental to the obtention of a homogenous cement paste. With a small mean particle size, the viscosity of the cement paste can be varied over a wide range. However, the powder requires a large amount of mixing liquid is required to obtain a kneadable paste. To obtain an adequate cement paste relative to its rheological properties, its setting time, and its mechanical properties after setting, an optimum must be found. This optimum depends on the application. For example, to obtain a tricalcium phosphate block with an open-porous structure, the use of a mixture of alpha tricalcium phosphate (rather large particle size) and a precipitated tricalcium phosphate (very small particle size) seems to be adequate.

To decrease the viscosity of the cement paste, steric stabilizers can be used. Their purpose is to decrease the interactions between the particles of the cement paste. One example is polyacrylic acid (PAA). This compound adsorbs on alpha-TCP particles in an aqueous solution, reducing the interparticle interactions, and hence decreasing the paste viscosity. The viscosity of a paste made of an aqueous solution and alpha-TCP particles can thus be drastically reduced by using small amounts of PAA (e.g. 1 weight-%). The viscosity can be increased by adding soluble polymers such as polysaccharides, e.g. hydroxypropylmethyl cellulose [CAS registry number 9004-65-3], hydroxypropylmethyl cellulose phthalate [CAS registry number 9050-31-1], hydroxyethyl cellulose [CAS registry number 9004-62-0], hydroxypropyl cellulose [CAS registry number 9004-64-2], tragacanth gum [CAS registry number 9000-65-1], sodium alginate [CAS registry number 9005-38-3], methyl cellulose [CAS registry number 9004-67-5], xanthan gum [CAS registry number 11138-66-2], hyaluronic acid [CAS registry number 9004-61-9], chitosan [CAS registry number 9012-76-4]. Small amounts (around 1 weight-%) are normally sufficient to reach the desired viscosity increase. The viscosity of the cement paste can also be controlled with the amount of mixing liquid or with the granulometry of the powders. It is clear that the viscosity of the cement paste increases when the amount of mixing liquid decreases. The use of powders with a very small particle size (e.g. 10 to 100 nanometers in diameter) enables the obtention of a very homogeneous and viscous paste.

The cement setting time is of importance. It should be easily controllable and most of the time decreased. This is the case for example for tetracalcium phosphate (TetCP; Ca/P=2.0, $Ca_4(PO_4)_2O$), dicalcium phosphate dihydrate (DCPD) and water mixtures which have very long setting times (more than an hour). Orthophosphate ions can be added to the aqueous solution leading to a large decrease of the setting time. The latter ions can be added as a salt (e.g. sodium-, potassium-, calcium-, or magnesium orthophosphate) or as an acid (phosphoric acid). Another possibility is to disperse a very fine powder in the cement paste which can act as nucleus for the crystal growth and thus accelerate the precipitation reaction. The powder should have in principle the same composition and crystal structure as that of the growing crystals. For example, very small hydroxyapatite particles (diameter in the nanometer range) are added to tetracalcium phosphate (TetCP; Ca/P= 2.0, $Ca_4(PO_4)_2O$), dicalcium phosphate dihydrate (DCPD) and water mixtures to decrease the setting time. The same strategy can be used in cements made of alpha-TCP and water. The setting time can be reduced by adding orthophosphate ions (e.g. $Na_2HPO_4$, $KHPO_4$ or $Ca(H_2PO_4)_2 \cdot H_2O$) into the cement formulation (either predissolved in the mixing solution or as solid particles), or by adding small calcium-deficient hydroxyapatite particles into the paste. In other cases, for example beta-TCP/MCPM/water mixtures, the setting time must be slightly increased. This can be done by means of pyrophosphate, citrate or sulphate ions. Actually, all inhibitors of DCPD crystal growth can be used as setting retarder, e.g. phosphocitrate ions, proteins or poly(acrylic acid).

The interfacial energy between the calcium phosphate hydraulic cement paste and the hydrophobic liquid plays an important role in enabling the obtention of an emulsion. A decrease of this interfacial energy is favourable. This decrease can be achieved by using suitable tensioactive agents. These agents have normally an amphipathic character, i.e. have a hydrophobic and a hydrophilic part, such as sodium dodecyl sulphate. Only minute amounts are necessary to reach a good effect (e.g. 0.001 weight-%). The use of a tensioactive agent eases the obtention of an emulsion and allows a good control of the droplet size. The main requirement for the hydrophobic liquid is to have very little to no mixing with the calcium phosphate hydraulic cement paste. Other factors of importance are the viscosity and the density of the liquid. The viscosity should match that of the calcium phosphate hydraulic cement paste, meaning that the viscosity should reach at least 100 mPa·s. Oils are a good choice. In principle, the problem in the choice of the hydrophobic liquid is that the viscosity of the latter liquid tends to be always too low. Castor oil and canula oil are probably the best choice when it comes to have a readily available, cheap and viscous oil. The density of the liquid must be large enough to prevent a too fast gravimetric phase separation. Values in the range of 0.5 to 5.0 g/ml are probably adequate, preferably close to 1.5 g/ml. The hydrophobic liquid can also be a cement paste in liquid form. Experiments done with polymethylmethacrylate (PMMA) cement have proved to give good results. In that case, the liquid monomer of methylmethacrylate (MMA) and the PMMA powder are initially mixed together and added to the calcium phosphate hydraulic cement paste. Liquid PMMA cement provides a good control of the pore size and volume, and enables (after burning out the hardened cement) the obtention of well-interconnected non-spherical pores in the calcium phosphate cement. However, the monomer of the PMMA cement is toxic and PMMA is not so easy remove. Among all hydrophobic liquids that were tested, the best results were obtained with highly-viscous paraffines and viscous oils such as canula oil and castor oil. As the viscosity of the latter liquids increase with a decrease of temperature, results were better at 4° C. than at 25° C.

Other hydrophobic liquids such as Tegosoft M and Triacetin were also tested. But both solutions have a rather low viscosity which prevents a good mixing with the cement. However, both are accepted for parenteral applications, implying that an injectable paste could be developed which could harden in vivo and have interconnected macropores.

It is of importance to control the size, the volume and the interconnectivity of the macropores in order to obtain an open macroporous calcium phosphate matrix. The volume can be controlled by the amount of hydrophobic liquid added to the calcium phosphate hydraulic cement paste. It can also be controlled by the addition of granules that can be dissolved or burned after cement hardening. The macropore size depends on the volume of hydrophobic liquid added to the cement paste. Normally, the larger this volume the larger the macropores. However, the use of tensioactive agents enables a good control of the macropore size. The macropore interconnectivity is related to the volume and the size of the macropores. The use of a tensioactive agent has a tendency to decrease the interconnectivity. A decrease of the viscosity of the hydrophilic/hydrophobic mixture has also a tendency to decrease the interconnectivity. The best way to get interconnected macropores is to have a mixture that sets very quickly, hence freezing the structure, and/or to have a rather viscous mixture. A favourable condition is to take a calcium phosphate hydraulic cement paste which has a viscosity at the limit between a plastic and a liquid state or which is thixotrope, i.e. has a viscosity decreasing with an increase in shear stresses.

After hardening, the calcium phosphate hydraulic cement paste has a rather high micro- or even nanoporosity. This volume can range from 25–30 volume-% to 80 volume-%. This volume depends on the amount of mixing liquid added to the calcium phosphate powders. The micropore volume can be reduced by sintering the calcium phosphate matrix. If the sintering conditions are well adjusted, the microporous volume should be close to 0%.

In a preferred embodiment of the invention the hydrophobic liquid can be added in two or more steps. By this method a first emulsion ("hydrophobic liquid in cement paste") is made and subsequently an "emulsion of the emulsion" is made by diluting the first emulsion into additional hydrophobic liquid. Such a double emulsion with water may be called a "water in oil in water double emulsion process".

EXAMPLE 1

8 g alpha-TCP, 1.2 g precipitated tricalcium phosphate, (this tricalcium phosphate is a calcium-deficient hydroxyapatite with the chemical composition $Ca_9(HPO_4)(PO_4)_5OH$; it is obtained by precipitation and is transformed into beta-TCP above 500–600° C.), 5.0 ml of a PAA 1% and Cremophor EL (polyethoxylated castor oil) 0.001% solution and 8.0 ml paraffine are mixed together for 4 minutes. The mixture is then poured into a mold and left to harden. After 12 hours, the hardened mixture is unmolded and left in water for 2 subsequent days to complete setting reaction. The sample is then sintered at 1250° C. for 4 hours. The composition of the final sample is beta-TCP. The sample has nice and large interconnected macropores. The overall porosity is 75%, 55% of pores being in the range of 200<d<500 microns and 18% of pores being in the range of 0.05<d<10 microns. The 2 remaining percents are not comprised in these two ranges. The interconnections have a diameter in the range of 100 to 300 microns.

EXAMPLE 2

1.1 g beta-TCP, 0.9 g MCPM, 0.02 g $Na_2H_2P_2O_2$, 0.8 ml $H_2O$, and 100 ml canula oil are stirred together for 10 minutes. The mixture is filtered and the granules—generated by the hardening of the hydraulic cement mixture—collected on the filter paper are sintered at 1100° C. for 2 hours. The granules collected after sintering are round, monodisperse and dense. They have a diameter in the range of 100 to 300 microns. The granules are made out of almost pure calcium pyrophosphate.

EXAMPLE 3

8 g a-TCP, 0.8 g precipitated tricalcium phosphate, 0.5 g CC, 6.0 ml of Cremophor EL 0.001% solution, and 8.0 ml Tegosoft M (isopropyl myristate $C_{17}H_{34}O_2$) are mixed together for 4 minutes. The mixture is then poured into a syringe and injected into a cavity. After hardening, the cavity is filled with an open macroporous calcium phosphate structure. As shown by x-ray diffraction and FTIR analysis, the calcium phosphate is a poorly-crystallized calcium-deficient carbonated hydroxyapatite.

What is claimed:

1. A composition comprising a hydraulic cement for implantation in a human or animal body, said hydraulic cement comprising a first component comprising a calcium source, and a second component comprising water, wherein:
   A) said composition comprises a third component comprising a hydrophobic liquid that is able to form an emulsion when admixed to said first and second components of said hydraulic cement;
   B) said composition hardens after mixing together of said three components by the action of said water with said first component;
   C) said second component further comprises a surfactant or emulsifier;
   D) said composition has a Ca/P molar ratio comprised between 1.0 and 20.0; and
   E) said second component further comprises an additive to control the cement setting time, said additive being either a liquid substance or a solid substance soluble in water and comprising a substance chosen from the group consisting of pyrophosphate, citrate, magnesium orthophosphate or polyphosphate ions, amino acids, peptides and proteins.

2. The composition according to claim 1, wherein said surfactant or emulsifier accelerates and stabilizes the formation of an emulsion.

3. The composition according to claim 2, wherein said surfactant or emulsifier is selected from the group consisting of:
   docusate sodium ($C_{20}H_{37}NaO_7S$), sodium lauryl sulfate ($C_{12}H_{25}NaO_4S$), stearic acid ($C_{17}H_{35}COOH$), alkyldimethyl(phenylmethyl)ammonium chloride, benzethonium chloride ($C_{27}H_{42}ClNO_2$), cetrimide ($C_{17}H_{38}BrN$), glycerin monooleate ($C_{21}H_{40}O_4$), polyoxyethylene (20) sorbitan monooleate ($C_{58}H_{114}O_{26}$), polyoxyethylene (4) sorbitan monolaurate ($C_{26}H_{50}O_{10}$), polyoxyethylene (20) sorbitan monopalmitate ($C_{62}H_{122}O_{26}$), polyoxyethylene (20) sorbitan monostearate ($C_{64}H_{126}O_{26}$), polyoxyethylene (4) sorbitan monostearate ($C_{32}H_{62}O_{10}$), polyoxyethylene (20) sorbitan tristearate ($C_{100}H_{194}O_{28}$), polyoxyethylene (20) sorbitan monooleate ($C_{64}H_{124}O_{26}$), polyoxyethylene (5) sorbitan monooleate ($C_{34}H_{64}O_{11}$), polyoxyethylene (20) sorbitan trioleate ($C_{100}H_{188}O_{28}$), polyoxyethylene (20) sorbitan monoisostearate ($C_{64}H_{126}O_{26}$), polyvinyl alcohol, sorbitan di-isostearate ($C_{42}H_{80}O_7$), sorbitan dioleate ($C_{42}H_{76}O_7$), sorbitan monoisostearate ($C_{24}H_{46}O_6$), sorbitan monolaurate ($C_{18}H_{34}O_6$), sorbitan monooleate ($C_{24}H_{44}O_6$), sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palpitate ($C_{19}H_{38}O_2$), lanolin, lanolin alcohols, hydrous lanolin, lecithin, triglycerides, monoethanolamine ($C_2H_7NO$), oleic acid ($C_{17}H_{33}COOH$), polyethylene glycol monocetyl ether, polyethylene glycol monostearyl ether, polyethylene glycol monolauryl ether, polyethylene glycol monooleyl ether, polyethoxylated castor oil, polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax, nonionic emulsifying wax, and sodium dodecyl sulphate ($NaC_{12}H_{25}SO_4$).

4. The composition according to claim 1, wherein the hydrophobic liquid is selected from the group consisting of:
   ricinoleic acid ($C_{17}H_{33}OCOOH$), linoleic acid ($C_{17}H_{31}COOH$), palmitic acid ($C_{15}H_{31}COOH$), palmitoleic acid ($C_{15}H_{29}COOH$), stearic acid ($C_{17}H_{35}COOH$), linolenic acid ($C_{17}H_{29}COOH$), arachidic acid ($C_{19}H_{39}COOH$), myristic acid ($C_{13}H_{27}COOH$), lauric acid ($C_{11}H_{23}COOH$), capric acid ($C_9H_{19}COOH$), caproic acid ($C_5H_{11}COOH$), oleic acid ($C_{17}H_{33}COOH$), caprylic acid ($C_7H_{15}COOH$), erucic acid ($C_{21}H_{41}COOH$), butyric acid ($C_3H_7COOH$), ethyl myristate ($C_{13}H_{27}COOC_2H_5$), ethyl oleate ($C_{17}H_{33}COOC_2H_5$), ethyl palmitate ($C_{15}H_{31}COOC_2H_5$), ethyl linoleate ($C_{17}H_{31}COOC_2H_5$), ethyl laurate ($C_{11}H_{23}COOC_2H_5$), ethyl linolenate ($C_{17}H_{29}COOC_2H_5$), ethyl stearate ($C_{17}H_{35}COOC_2H_5$), ethyl arachidate ($C_{19}H_{39}COOC_2H_5$), ethyl caprilate ($C_7H_{15}COOC_2H_5$), ethyl caprate ($C_9H_{19}COOC_2H_5$), ethyl caproate ($C_5H_{11}COOC_2H_5$), ethyl butyrate ($C_3H_7COOC_2H_5$), triacetin ($C_9H_{14}O_6$), alpha tocopherol ($C_{29}H_{50}O_2$), beta tocopherol ($C_{28}H_{48}O_2$), delta tocopherol ($C_{27}H_{46}O_2$), gamma tocopherol ($C_{28}H_{48}O_2$), benzyl alcohol ($C_7H_8O$), benzyl benzoate ($C_{14}H_{12}O_2$), methylphenol ($C_7H_8O$), di-n-butyl sebacate ($C_{18}H_{34}O_4$), diethylphthalate ($C_{12}H_{14}O_4$), glyceryl monooleate ($C_{21}H_{40}O_4$), lecithin, triglycerides, mineral oil, petrolatum, and liquid paraffines.

5. The composition according to claim 1, wherein the hydrophobic liquid is a vegetable oil selected from the group consisting of:
   canola oil, corn oil, cottonseed oil, peanut oil, sesame oil, castor oil, and soybean oil.

6. The composition according to claim 1, wherein said first and second component correspond together to 0.001 to 90.000 volume-% of the total weight of the three components together.

7. The composition according to claim 6, wherein said first and second component correspond together to 0.1 to 80.0 volume-% of the total weight of the three components together.

8. The composition according to claim 1, wherein said third component corresponds to 10 to 90 volume-% of the total weight of the three components together.

9. The composition according to claim 8, wherein said third component corresponds to 20 to 80 volume-% of the total weight of the three components together.

10. The composition according to claim 1, wherein the composition is obtained by combining 40 to 70 volume-% of said first and second components with 30 to 60 volume-% of said third component.

11. The composition according to claim 1, wherein the composition has a Ca/P molar ratio comprised between 1.0 and 2.0.

12. The composition according to claim 11, wherein the composition has a Ca/P molar ratio comprised between 1.0 to 1.67.

13. The composition according to claim 12, wherein the composition has a Ca/P molar ratio comprised between 1.45 to 1.60.

14. The composition according to claim 1, wherein said first component comprises calcium sulphate hemihydrate [$CaSO_4\text{-}½H_2O$], calcium pyrophosphate [$Ca_2P_2O_7$], calcium carbonate [$CaCO_3$], monocalcium phosphate monohydrate [$Ca(H_2PO_4)_2·H_2O$], monocalcium phosphate [$Ca(H_2PO_4)_2$], anhydrous dicalcium phosphate [$CaHPO_4$], dicalcium phosphate dihydrate [$CaHPO_4·2H_2O$], octocalcium phosphate [Ca$_8$H$_2$(PO$_4$)$_6$$5H$_2$O], alpha-tricalcium phosphate [alpha-Ca$_3$(PO$_4$)$_2$], beta-tricalcium phosphate [beta-Ca$_3$(PO$_4$)$_2$], hydroxyapatite [Ca$_5$(PO$_4$)$_3$OH], tetracalcium phosphate [Ca$_4$(PO$_4$)$_2$O], calcium-deficient hydroxyapatite, fluoroapatite (Ca$_5$(PO$_4$)$_3$F], amorphous calcium phosphate, oxyapatite [Ca$_{10}$(PO$_4$)$_6$O], calcium oxide and calcium hydroxide [Ca(OH$_2$] or a mixture of some or all of them.

15. The composition according to claim 1, wherein said second component further comprises sulfuric acid [H$_2$SO$_4$], phosphoric acid [H$_3$PO$_4$], citric acid or a mixture of them.

16. The composition according to claim 1, wherein said second component further comprises an additive to control the cement rheology.

17. The composition according to claim 16, wherein said additive to control the cement rheology is a polymer.

18. The composition according to claim 17, wherein said polymer is a polysaccharide.

19. The composition according to claim 18, wherein said polysaccharide is chosen from the group consisting of: hydroxypropylmethyl cellulose, hydroxypropylmethyl cellulose phthalate, hydroxyethyl cellulose, hydroxypropyl cellulose, tragacanth gum, sodium alginate, methyl cellulose, xanthan gum, hyaluronic acid, and chitosan.

20. A composition comprising a hydraulic cement for implantation in a human or animal body, said hydraulic cement comprising a first component comprising a calcium source, and a second component comprising water, wherein:
A) said composition comprises a third component comprising a hydrophobic liquid that is able to form an emulsion when admixed to said first and second components of said hydraulic cement;
B) said composition hardens after mixing together of said three components by the action of said water with said first component;
C) said second component further comprises a surfactant or emulsifier;
D) said composition has a Ca/P molar ratio comprised between 1.0 and 20.0;
E) said second component further comprises an additive to control the cement setting time; and
F) said second component further comprises a polymer to control the cement rheology, wherein said polymer is chosen from the group consisting of: polyvinyl alcohol and propylene glycol alginate.

21. A composition comprising a hydraulic cement for implantation in a human or animal body, said hydraulic cement comprising a first component comprising a calcium source, and a second component comprising water, wherein:
A) said composition comprises a third component comprising a hydrophobic liquid that is able to form an emulsion when admixed to said first and second components of said hydraulic cement;
B) said composition hardens after mixing together of said three components by the action of said water with said first component;
C) said second component further comprises a surfactant or emulsifier;
D) said composition has a Ca/P molar ratio comprised between 1.0 and 20.0;
E) said second component further comprises an additive to control the cement setting time; and
F) said second component further comprises a polymer to sterically stabilize the first component, wherein said polymer is a polyacrylic acid.

22. The composition according to claim 1, wherein a setting time of the cement upon mixing of said three components is between about 1 and 600 minutes.

23. The composition according to claim 22, wherein said setting time is between about 2 and 60 minutes.

24. The composition according to claim 23, wherein setting time is between about 5 and 20 minutes.

25. The composition according to claim 1, wherein the volume of the second component VL of the cement is in the range of 0.5 VT<VL<10 VT, where VT is the volume of the first component.

26. The composition according to claim 1, wherein the volume of the second component VL of the cement is in the range of 0.8 VT<VL<2.0 VT, where VT is the volume of the first component.

27. The composition according to claim 1, wherein the third component has a viscosity SHS of between about 0.01 SC<SHS<100.00 SC, where SC is a viscosity of the mixture resulting from the first and second component.

28. The composition according to claim 1, wherein the hydrophobic liquid has a viscosity comprised between 0.01 and 100,000 mPa·s at a temperature in a range between about 0° C. to 55° C.

29. The composition according to claim 1, wherein the hydrophobic liquid has a density comprised between 0.2 and 10.0 g/cm$^3$.

30. The composition according to claim 1, wherein the composition comprises granules whose diameter is at least 10 times larger than an average diameter of the particles of the first component.

31. A composition comprising a hydraulic cement for implantation in a human or animal body, said hydraulic cement comprising a first component comprising a calcium source, and a second component comprising water, wherein:
A) said composition comprises a third component comprising a hydrophobic liquid that is able to form an emulsion when admixed to said first and second components of said hydraulic cement;
B) said composition hardens after mixing together of said three components by the action of said water with said first component;
C) said second component further comprises a surfactant or emulsifier;
D) said composition has a Ca/P molar ratio comprised between 1.0 and 20.0;
E) said second component further comprises an additive to control the cement setting time; and
F) said composition comprises granules whose diameter is at least 10 times larger than an average diameter of the particles of the first component, wherein the granules have an average diameter in the range of 1 mm to 3 mm.

32. The composition according to claim 30, wherein the granules are made out of calcium phosphate.

33. The composition according to claim 30, wherein the granules are made out of polymer.

34. The composition according to claim 30, wherein the granules are made out of bioglass.

35. The composition according to claim 1, wherein the hardened cement paste comprises calcium-deficient hydroxyapatite [Ca$_{10-x}$(HPO$_4$)$_x$(PO$_4$)$_{6-x}$(OH)$_{2-x}$] with $0 \leq x \leq 2$.

36. The composition according to claim 1, wherein the hardened cement paste comprises dicalcium phosphate dihydrate [CaHPO$_4$·2H$_2$O].

37. A composition comprising a hydraulic cement for implantation in a human or animal body, said hydraulic cement comprising a first component comprising a calcium source, and a second component comprising water, wherein:
- A) said composition comprises a third component comprising a hydrophobic liquid that is able to form an emulsion when admixed to said first and second components of said hydraulic cement;
- B) said composition hardens after mixing together of said three components by the action of said water with said first component;
- C) said second component further comprises a surfactant or emulsifier;
- D) said composition has a Ca/P molar ratio comprised between 1.0 and 20.0;
- E) said second component further comprises an additive to control the cement setting time; and
- F) wherein the first component comprises beta-tricalcium phosphate and a further substance selected from the group consisting of: monocalcium phosphate monohydrate $[Ca(H_2PO_4)_2 \cdot H_2O]$, monocalcium phosphate $[Ca(H_2PO_4)_2]$, and phosphoric acid $[H_3PO_4]$.

38. The composition according to claim 1, wherein the first component comprises alpha-tricalcium phosphate.

39. The composition according to claim 38, wherein the first component further comprises a precipitated calcium phosphate.

40. The composition according to claim 39, wherein said precipitated calcium phosphate has a Ca/P molar ratio of 1.50±0.02.

41. The composition according to claim 1, wherein the mixture comprises pharmaceutically or physiologically active substances, antibiotics, anti-inflammatory drugs, peptides, and proteins.

42. The composition according to claim 1, wherein the hydrophobic liquid is an autopolymerizable cement that hardens with time based on methacrylate.

43. A method for producing a porous calcium-containing matrix for use in a human or animal body, comprising the steps of:
- emulsifying a freshly mixed calcium-containing hydraulic cement paste and a hydrophobic liquid, wherein the hydrophobic liquid is the discontinuous phase and the freshly mixed calcium-containing hydraulic cement paste is the continuous phase;
- allowing the freshly mixed calcium-containing hydraulic cement paste to harden to thereby entrap the hydrophobic liquid in a hardened cement mixture; and
- removing the hydrophobic liquid from the hardened cement mixture to form a porous calcium-containing matrix.

44. The method according to claim 43, wherein said hydrophobic liquid is added in several steps to said freshly mixed calcium-containing hydraulic cement paste.

45. The method according to claim 43, wherein the hydrophobic liquid is removed from the hardened cement mixture by washing, freeze-drying, evaporation, thermolysis or a combination of these procedures.

46. The method according to claim 43, wherein the hardened cement mixture is sintered.

47. The composition according to claim 20, wherein said surfactant or emulsifier is selected from the group consisting of:
docusate sodium $(C_{20}H_{37}NaO_7S)$, sodium lauryl sulfate $(C_{12}H_{25}NaO_4S)$, stearic acid $(C_{17}H_{35}COOH)$, alkyldimethyl(phenylmethyl)ammonium chloride, benzethonium chloride $(C_{27}H_{42}ClNO_2)$, cetrimide $(C_{17}H_{38}BrN)$, glycerin monooleate $(C_{21}H_{40}O_4)$, polyoxyethylene (20) sorbitan monooleate $(C_{58}H_{114}O_{26})$, polyoxyethylene (4) sorbitan monolaurate $(C_{26}H_{50}O_{10})$, polyoxyethylene (20) sorbitan monopalmitate $(C_{62}H_{122}O_{26})$, polyoxyethylene (20) sorbitan monostearate $(C_{64}H_{126}O_{26})$, polyoxyethylene (4) sorbitan monostearate $(C_{32}H_{62}O_{10})$, polyoxyethylene (20) sorbitan tristearate $(C_{100}H_{194}O_{28})$, polyoxyethylene (20) sorbitan monooleate $(C_{64}H_{124}O_{26})$, polyoxyethylene (5) sorbitan monooleate $(C_{34}H_{64}O_{11})$, polyoxyethylene (20) sorbitan trioleate $(C_{100}H_{188}O_{28})$, polyoxyethylene (20) sorbitan monoisostearate $(C_{64}H_{126}O_{26})$, polyvinyl alcohol, sorbitan di-isostearate $(C_{42}H_{80}O_7)$, sorbitan dioleate $(C_{42}H_{76}O_7)$, sorbitan monoisostearate $(C_{24}H_{46}O_6)$, sorbitan monolaurate $(C_{18}H_{34}O_6)$, sorbitan monooleate $(C_{24}H_{44}O_6)$, sorbitan monopalmitate $(C_{22}H_{42}O_6)$, sorbitan monostearate $(C_{24}H_{46}O_6)$, sorbitan sesqui-isostearate $(C_{33}H_{63}O_{6.5})$, sorbitan sesquioleate $(C_{33}H_{63}O_{6.5})$, sorbitan sesquistearate $(C_{33}H_{63}O_{6.5})$, sorbitan tri-isostearate $(C_{33}H_{63}O_{6.5})$, sorbitan trioleate $(C_{33}H_{63}O_{6.5})$, sorbitan tristearate $(C_{33}H_{63}O_{6.5})$, glyceryl monooleate $(C_{21}H_{40}O_4)$, isopropyl myristate $(C_{17}H_{34}O_2)$, isopropyl palpitate $(C_{19}H_{38}O_2)$, lanolin, lanolin alcohols, hydrous lanolin, lecithin, triglycerides, monoethanolamine $(C_2H_7NO)$, oleic acid $(C_{17}H_{33}COOH)$, polyethylene glycol monocetyl ether, polyethylene glycol monostearyl ether, polyethylene glycol monolauryl ether, polyethylene glycol monooleyl ether, polyethoxylated castor oil, polyoxyl 40 stearate $(C_{98}H_{196}O_{42})$, polyoxyl 50 stearate $(C_{118}H_{236}O_{52})$, triethanolamine $(C_6H_{15}NO_3)$, anionic emulsifying wax, nonionic emulsifying wax, and sodium dodecyl sulphate $(NaC_{12}H_{25}SO_4)$.

48. The composition according to claim 20, wherein the hydrophobic liquid is selected from the group consisting of:
ricinoleic acid $(C_{17}H_{33}OCOOH)$, linoleic acid $(C_{17}H_{31}COOH)$, palmitic acid $(C_{15}H_{31}COOH)$, palmitoleic acid $(C_{15}H_{29}COOH)$, stearic acid $(C_{17}H_{35}COOH)$, linolenic acid $(C_{17}H_{29}COOH)$, arachidic acid $(C_{19}H_{39}COOH)$, myristic acid $(C_{13}H_{27}COOH)$, lauric acid $(C_{11}H_{23}COOH)$, capric acid $(C_9H_{19}COOH)$, caproic acid $(C_5H_{11}COOH)$, oleic acid $(C_{17}H_{33}COOH)$, caprylic acid $(C_7H_{15}COOH)$, erucic acid $(C_{21}H_{41}COOH)$, butyric acid $(C_3H_7COOH)$, ethyl myristate $(C_{13}H_{27}COOC_2H_5)$, ethyl oleate $(C_{17}H_{33}COOC_2H_5)$, ethyl palmitate $(C_{15}H_{31}COOC_2H_5)$, ethyl linoleate $(C_{17}H_{31}COOC_2H_5)$, ethyl laurate $(C_{11}H_{23}COOC_2H_5)$, ethyl linolenate $(C_{17}H_{29}COOC_2H_5)$, ethyl stearate $(C_{17}H_{35}COOC_2H_5)$, ethyl arachidate $(C_{19}H_{39}COOC_2H_5)$, ethyl caprilate $(C_7H_{15}COOC_2H_5)$, ethyl caprate $(C_9H_{19}COOC_2H_5)$, ethyl caproate $(C_5H_{11}COOC_2H_5)$, ethyl butyrate $(C_3H_7COOC_2H_5)$, triacetin $(C_9H_{14}O_6)$, alpha tocopherol $(C_{29}H_{50}O_2)$, beta tocopherol $(C_{28}H_{48}O_2)$, delta tocopherol $(C_{27}H_{46}O_2)$, gamma tocopherol $(C_{28}H_{48}O_2)$, benzyl alcohol $(C_7H_8O)$, benzyl benzoate $(C_{14}H_{12}O_2)$, methylphenol $(C_7H_8O)$, di-n-butyl sebacate $(C_{18}H_{34}O_4)$, diethylphthalate $(C_{12}H_{14}O_4)$, glyceryl monooleate $(C_{21}H_{40}O_4)$, lecithin, triglycerides, mineral oil, petrolatum, and liquid paraffines.

49. The composition according to claim 20, wherein the hydrophobic liquid is a vegetable oil selected from the group consisting of:
canola oil, corn oil, cottonseed oil, peanut oil, sesame oil, castor oil, and soybean oil.

50. The composition according to claim 20, wherein said first component comprises calcium sulphate hemihydrate

[CaSO$_4$-½H$_2$O], calcium pyrophosphate [Ca$_2$P$_2$O$_7$], calcium carbonate [CaCO$_3$], monocalcium phosphate monohydrate [Ca(H$_2$PO$_4$)$_2$$H$_2$O], monocalciumn phosphate [Ca(H$_2$PO$_4$)$_2$], anhydrous dicalcium phosphate [CaHPO$_4$], dicalcium phosphate dihydrate [CaHPO$_4$$2H$_2$O], octocalcium phosphate [Ca$_8$H$_2$(PO$_4$)$_6$$5H$_2$O], alpha-tricalcium phosphate [alpha-Ca$_3$(PO$_4$)$_2$], beta-tricalcium phosphate [beta-Ca$_3$(PO$_4$)$_2$], hydroxyapatite [Ca$_5$(PO$_4$)$_3$OH], tetracalcium phosphate [Ca$_4$(PO$_4$)$_2$O], calcium-deficient hydroxyapatite, fluoroapatite (Ca$_5$(PO$_4$)$_3$F], amorphous calcium phosphate, oxyapatite [Ca$_{10}$(PO$_4$)$_6$O], calcium oxide and calcium hydroxide [Ca(OH$_2$] or a mixture of some or all of them.

51. The composition according to claim 21, wherein said surfactant or emulsifier is selected from the group consisting of:

docusate sodium (C$_{20}$H$_{37}$NaO$_7$S), sodium lauryl sulfate (C$_{12}$H$_{25}$NaO$_4$S), stearic acid (C$_{17}$H$_{35}$COOH), alkyldimethyl(phenylmethyl)ammonium chloride, benzethonium chloride (C$_{27}$H$_{42}$ClNO$_2$), cetrimide (C$_{17}$H$_{38}$BrN), glycerin monooleate (C$_{21}$H$_{40}$O$_4$), polyoxyethylene (20) sorbitan monooleate (C$_{58}$H$_{114}$O$_{26}$), polyoxyethylene (4) sorbitan monolaurate (C$_{26}$H$_{50}$O$_{10}$), polyoxyethylene (20) sorbitan monopalmitate (C$_{62}$H$_{122}$O$_{26}$), polyoxyethylene (20) sorbitan monostearate (C$_{64}$H$_{126}$O$_{26}$), polyoxyethylene (4) sorbitan monostearate (C$_{32}$H$_{62}$O$_{10}$), polyoxyethylene (20) sorbitan tristearate (C$_{100}$H$_{194}$O$_{28}$), polyoxyethylene (20) sorbitan monooleate (C$_{64}$H$_{124}$O$_{26}$), polyoxyethylene (5) sorbitan monooleate (C$_{34}$H$_{64}$O$_{11}$), polyoxyethylene (20) sorbitan trioleate (C$_{100}$H$_{188}$O$_{28}$), polyoxyethylene (20) sorbitan monoisostearate (C$_{64}$H$_{126}$O$_{26}$), polyvinyl alcohol, sorbitan di-isostearate (C$_{42}$H$_{80}$O$_7$), sorbitan dioleate (C$_{42}$H$_{76}$O$_7$), sorbitan monoisostearate (C$_{24}$H$_{46}$O$_6$), sorbitan monolaurate (C$_{18}$H$_{34}$O$_6$), sorbitan monooleate (C$_{24}$H$_{44}$O$_6$), sorbitan monopalmitate (C$_{22}$H$_{42}$O$_6$), sorbitan monostearate (C$_{24}$H$_{46}$O$_6$), sorbitan sesqui-isostearate (C$_{33}$H$_{63}$O$_{6.5}$), sorbitan sesquioleate (C$_{33}$H$_{63}$O$_{6.5}$), sorbitan sesquistearate (C$_{33}$H$_{63}$O$_{6.5}$), sorbitan tri-isostearate (C$_{33}$H$_{63}$O$_{6.5}$), sorbitan trioleate (C$_{33}$H$_{63}$O$_{6.5}$), sorbitan tristearate (C$_{33}$H$_{63}$O$_{6.5}$), glyceryl monooleate (C$_{21}$H$_{40}$O$_4$), isopropyl myristate (C$_{17}$H$_{34}$O$_2$), isopropyl palpitate (C$_{19}$H$_{38}$O$_2$), lanolin, lanolin alcohols, hydrous lanolin, lecithin, triglycerides, monoethanolamine (C$_2$H$_7$NO), oleic acid (C$_{17}$H$_{33}$COOH), polyethylene glycol monocetyl ether, polyethylene glycol monostearyl ether, polyethylene glycol monolauryl ether, polyethylene glycol monooleyl ether, polyethoxylated castor oil, polyoxyl 40 stearate (C$_{98}$H$_{196}$O$_{42}$), polyoxyl 50 stearate (C$_{118}$H$_{236}$O$_{52}$), triethanolamine (C$_6$H$_{15}$NO$_3$), anionic emulsifying wax, nonionic emulsifying wax, and sodium dodecyl sulphate (NaC$_{12}$H$_{25}$SO$_4$).

52. The composition according to claim 21, wherein the hydrophobic liquid is selected from the group consisting of:

ricinoleic acid (C$_{17}$H$_{33}$OCOOH), linoleic acid (C$_{17}$H$_{31}$COOH), palmitic acid (C$_{15}$H$_{31}$COOH), palmitoleic acid (C$_{15}$H$_{29}$COOH), stearic acid (C$_{17}$H$_{35}$COOH), linolenic acid (C$_{17}$H$_{29}$COOH), arachidic acid (C$_{19}$H$_{39}$COOH), myristic acid (C$_{13}$H$_{27}$COOH), lauric acid (C$_{11}$H$_{23}$COOH), capric acid (C$_9$H$_{19}$COOH), caproic acid (C$_5$H$_{11}$COOH), oleic acid (C$_{17}$H$_{33}$COOH), caprylic acid (C$_7$H$_{15}$COOH), erucic acid (C$_{21}$H$_{41}$COOH), butyric acid (C$_3$H$_7$COOH), ethyl myristate (C$_{13}$H$_{27}$COOC$_2$H$_5$), ethyl oleate (C$_{17}$H$_{33}$COOC$_2$H$_5$), ethyl palmitate (C$_{15}$H$_{31}$COOC$_2$H$_5$), ethyl linoleate (C$_{17}$H$_{31}$COOC$_2$H$_5$), ethyl laurate (C$_{11}$H$_{23}$COOC$_2$H$_5$), ethyl linolenate (C$_{17}$H$_{29}$COOC$_2$H$_5$), ethyl stearate (C$_{17}$H$_{35}$COOC$_2$H$_5$), ethyl arachidate (C$_{19}$H$_{39}$COOC$_2$H$_5$), ethyl caprilate (C$_7$H$_{15}$COOC$_2$H$_5$), ethyl caprate (C$_9$H$_{19}$COOC$_2$H$_5$), ethyl caproate (C$_5$H$_{11}$COOC$_2$H$_5$), ethyl butyrate (C$_3$H$_7$COOC$_2$H$_5$), triacetin (C$_9$H$_{14}$O$_6$), alpha tocopherol (C$_{29}$H$_{50}$O$_2$), beta tocopherol (C$_{28}$H$_{48}$O$_2$), delta tocopherol (C$_{27}$H$_{46}$O$_2$), gamma tocopherol (C$_{28}$H$_{48}$O$_2$), benzyl alcohol (C$_7$H$_8$O), benzyl benzoate (C$_{14}$H$_{12}$O$_2$), methylphenol (C$_7$H$_8$O), di-n-butyl sebacate (C$_{18}$H$_{34}$O$_4$), diethylphthalate (C$_{12}$H$_{14}$O$_4$), glyceryl monooleate (C$_{21}$H$_{40}$O$_4$), lecithin, triglycerides, mineral oil, petrolatum, and liquid paraffines.

53. The composition according to claim 21, wherein the hydrophobic liquid is a vegetable oil selected from the group consisting of:

canola oil, corn oil, cottonseed oil, peanut oil, sesame oil, castor oil, and soybean oil.

54. The composition according to claim 21, wherein said first component comprises calcium sulphate hemihydrate [CaSO$_4$-½H$_2$O], calcium pyrophosphate [Ca$_2$P$_2$O$_7$], calcium carbonate [CaCO$_3$], monocalcium phosphate monohydrate [Ca(H$_2$PO$_4$)$_2$$H$_2$O], monocalcium phosphate [Ca(H$_2$PO$_4$)$_2$], anhydrous dicalcium phosphate [CaHPO$_4$], dicalcium phosphate dihydrate [CaHPO$_4$$2H$_2$O], octocalcium phosphate [Ca$_8$H$_2$(PO$_4$)$_6$$5H$_2$O], alpha-tricalcium phosphate [alpha-Ca$_3$(PO$_4$)$_2$], beta-tricalcium phosphate [beta-Ca$_3$(PO$_4$)$_2$], hydroxyapatite [Ca$_5$(PO$_4$)$_3$OH], tetracalcium phosphate [Ca$_4$(PO$_4$)$_2$O], calcium-deficient hydroxyapatite, fluoroapatite (Ca$_5$(PO$_4$)$_3$F], amorphous calcium phosphate, oxyapatite [Ca$_{10}$(PO$_4$)$_6$O], calcium oxide and calcium hydroxide [Ca(OH$_2$] or a mixture of some or all of them.

55. The composition according to claim 31, wherein said surfactant or emulsifier is selected from the group consisting of:

docusate sodium (C$_{20}$H$_{37}$NaO$_7$S), sodium lauryl sulfate (C$_{12}$H$_{25}$NaO$_4$S), stearic acid (C$_{17}$H$_{35}$COOH), alkyldimethyl(phenylmethyl)ammonium chloride, benzethonium chloride (C$_{27}$H$_{42}$ClNO$_2$), cetrimide (C$_{17}$H$_{38}$BrN), glycerin monooleate (C$_{21}$H$_{40}$O$_4$), polyoxyethylene (20) sorbitan monooleate (C$_{58}$H$_{114}$O$_{26}$), polyoxyethylene (4) sorbitan monolaurate (C$_{26}$H$_{50}$O$_{10}$), polyoxyethylene (20) sorbitan monopalmitate (C$_{62}$H$_{122}$O$_{26}$), polyoxyethylene (20) sorbitan monostearate (C$_{64}$H$_{126}$O$_{26}$), polyoxyethylene (4) sorbitan monostearate (C$_{32}$H$_{62}$O$_{10}$), polyoxyethylene (20) sorbitan tristearate (C$_{100}$H$_{194}$O$_{28}$), polyoxyethylene (20) sorbitan monooleate (C$_{64}$H$_{124}$O$_{26}$), polyoxyethylene (5) sorbitan monooleate (C$_{34}$H$_{64}$O$_{11}$), polyoxyethylene (20) sorbitan trioleate (C$_{100}$H$_{188}$O$_{28}$), polyoxyethylene (20) sorbitan monoisostearate (C$_{64}$H$_{126}$O$_{26}$), polyvinyl alcohol, sorbitan di-isostearate (C$_{42}$H$_{80}$O$_7$), sorbitan dioleate (C$_{42}$H$_{76}$O$_7$), sorbitan monoisostearate (C$_{24}$H$_{46}$O$_6$), sorbitan monolaurate (C$_{18}$H$_{34}$O$_6$), sorbitan monooleate (C$_{24}$H$_{44}$O$_6$), sorbitan monopalmitate (C$_{22}$H$_{42}$O$_6$), sorbitan monostearate (C$_{24}$H$_{46}$O$_6$), sorbitan sesqui-isostearate (C$_{33}$H$_{63}$O$_{6.5}$), sorbitan sesquioleate (C$_{33}$H$_{63}$O$_{6.5}$), sorbitan sesquistearate (C$_{33}$H$_{63}$O$_{6.5}$), sorbitan tri-isostearate (C$_{33}$H$_{63}$O$_{6.5}$), sorbitan trioleate (C$_{33}$H$_{63}$O$_{6.5}$), sorbitan tristearate (C$_{33}$H$_{63}$O$_{6.5}$), glyceryl monooleate (C$_{21}$H$_{40}$O$_4$), isopropyl myristate (C$_{17}$H$_{34}$O$_2$), isopropyl palpitate (C$_{19}$H$_{38}$O$_2$), lanolin, lanolin alcohols, hydrous lanolin, lecithin, triglycerides, monoethanolamine ($C_2H_7NO$), oleic acid ($C_{17}H_{33}COOH$), polyethylene glycol monocetyl ether, polyethylene glycol monostearyl ether, polyethylene glycol monolauryl ether, polyethylene glycol monooleyl ether, polyethoxylated castor oil, polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax, nonionic emulsifying wax, and sodium dodecyl sulphate ($NaC_{12}H_{25}SO_4$).

56. The composition according to claim 31, wherein the hydrophobic liquid is selected from the group consisting of:
ricinoleic acid ($C_{17}H_{33}OCOOH$), linoleic acid ($C_{17}H_{31}COOH$), palmitic acid ($C_{15}H_{31}COOH$), palmitoleic acid ($C_{15}H_{29}COOH$), stearic acid ($C_{17}H_{35}COOH$), linolenic acid ($C_{17}H_{29}COOH$), arachidic acid ($C_{19}H_{39}COOH$), myristic acid ($C_{13}H_{27}COOH$), lauric acid ($C_{11}H_{23}COOH$), capric acid ($C_9H_{19}COOH$), caproic acid ($C_5H_{11}COOH$), oleic acid ($C_{17}H_{33}COOH$), caprylic acid ($C_7H_{15}COOH$), erucic acid ($C_{21}H_{41}COOH$), butyric acid ($C_3H_7COOH$), ethyl myristate ($C_{13}H_{27}COOC_2H_5$), ethyl oleate ($C_{17}H_{33}COOC_2H_5$), ethyl palmitate ($C_{15}H_{31}COOC_2H_5$), ethyl linoleate ($C_{17}H_{31}COOC_2H_5$), ethyl laurate ($C_{11}H_{23}COOC_2H_5$), ethyl linolenate ($C_{17}H_{29}COOC_2H_5$), ethyl stearate ($C_{17}H_{35}COOC_2H_5$), ethyl arachidate ($C_{19}H_{39}COOC_2H_5$), ethyl caprilate ($C_7H_{15}COOC_2H_5$), ethyl caprate ($C_9H_{19}COOC_2H_5$), ethyl caproate ($C_5H_{11}COOC_2H_5$), ethyl butyrate ($C_3H_7COOC_2H_5$), triacetin ($C_9H_{14}O_6$), alpha tocopherol ($C_{29}H_{50}O_2$), beta tocopherol ($C_{28}H_{48}O_2$), delta tocopherol ($C_{27}H_{46}O_2$), gamma tocopherol ($C_{28}H_{48}O_2$), benzyl alcohol ($C_7H_8O$), benzyl benzoate ($C_{14}H_{12}O_2$), methylphenol ($C_7H_8O$), di-n-butyl sebacate ($C_{18}H_{34}O_4$), diethylphthalate ($C_{12}H_{14}O_4$), glyceryl monooleate ($C_{21}H_{40}O_4$), lecithin, triglycerides, mineral oil, petrolatum, and liquid paraffines.

57. The composition according to claim 31, wherein the hydrophobic liquid is a vegetable oil selected from the group consisting of:
canola oil, corn oil, cottonseed oil, peanut oil, sesame oil, castor oil, and soybean oil.

58. The composition according to claim 31, wherein said first component comprises calcium sulphate hemihydrate [$CaSO_4$-½$H_2O$], calcium pyrophosphate [$Ca_2P_2O_7$], calcium carbonate [$CaCO_3$], monocalcium phosphate monohydrate [$Ca(H_2PO_4)_2$$H_2O$], monocalcium phosphate [$Ca(H_2PO_4)_2$], anhydrous dicalcium phosphate [$CaHPO_4$], dicalcium phosphate dihydrate [$CaHPO_4$$2H_2O$], octocalcium phosphate [$Ca_8H_2(PO_4)_6$$5H_2O$], alpha-tricalcium phosphate [alpha-$Ca_3(PO_4)_2$], beta-tricalcium phosphate [beta-$Ca_3(PO_4)_2$], hydroxyapatite [$Ca_5(PO_4)_3OH$], tetracalcium phosphate [$Ca_4(PO_4)_2O$], calcium-deficient hydroxyapatite, fluoroapatite ($Ca_5(PO_4)_3F$), amorphous calcium phosphate, oxyapatite [$Ca_{10}(PO_4)_6O$], calcium oxide and calcium hydroxide [$Ca(OH_2$] or a mixture of some or all of them.

59. The composition according to claim 37, wherein said surfactant or emulsifier is selected from the group consisting of:
docusate sodium ($C_{20}H_{37}NaO_7S$), sodium lauryl sulfate ($C_{12}H_{25}NaO_4S$), stearic acid ($C_{17}H_{35}COOH$), alkyldimethyl(phenylmethyl)ammonium chloride, benzethonium chloride ($C_{27}H_{42}ClNO_2$), cetrimide ($C_{17}H_{38}BrN$), glycerin monooleate ($C_{21}H_{40}O_4$), polyoxyethylene (20) sorbitan monooleate ($C_{58}H_{114}O_{26}$), polyoxyethylene (4) sorbitan monolaurate ($C_{26}H_{50}O_{10}$), polyoxyethylene (20) sorbitan monopalmitate ($C_{62}H_{122}O_{26}$), polyoxyethylene (20) sorbitan monostearate ($C_{64}H_{126}O_{26}$), polyoxyethylene (4) sorbitan monostearate ($C_{32}H_{62}O_{10}$), polyoxyethylene (20) sorbitan tristearate ($C_{100}H_{194}O_{28}$), polyoxyethylene (20) sorbitan monooleate ($C_{64}H_{124}O_{26}$), polyoxyethylene (5) sorbitan monooleate ($C_{34}H_{64}O_{11}$), polyoxyethylene (20) sorbitan trioleate ($C_{100}H_{188}O_{28}$), polyoxyethylene (20) sorbitan monoisostearate ($C_{64}H_{126}O_{26}$), polyvinyl alcohol, sorbitan di-isostearate ($C_{42}H_{80}O_7$), sorbitan dioleate ($C_{42}H_{76}O_7$), sorbitan monoisostearate ($C_{24}H_{46}O_6$), sorbitan monolaurate ($C_{18}H_{34}O_6$), sorbitan monooleate ($C_{24}H_{44}O_6$), sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palpitate ($C_{19}H_{38}O_2$), lanolin, lanolin alcohols, hydrous lanolin, lecithin, triglycerides, monoethanolamine ($C_2H_7NO$), oleic acid ($C_{17}H_{33}COOH$), polyethylene glycol monocetyl ether, polyethylene glycol monostearyl ether, polyethylene glycol monolauryl ether, polyethylene glycol monooleyl ether, polyethoxylated castor oil, polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax, nonionic emulsifying wax, and sodium dodecyl sulphate ($NaC_{12}H_{25}SO_4$).

60. The composition according to claim 39, wherein the hydrophobic liquid is selected from the group consisting of:
ricinoleic acid ($C_{17}H_{33}OCOOH$), linoleic acid ($C_{17}H_{31}COOH$), palmitic acid ($C_{15}H_{31}COOH$), palmitoleic acid ($C_{15}H_{29}COOH$), stearic acid ($C_{17}H_{35}COOH$), linolenic acid ($C_{17}H_{29}COOH$), arachidic acid ($C_{19}H_{39}COOH$), myristic acid ($C_{13}H_{27}COOH$), lauric acid ($C_{11}H_{23}COOH$), capric acid ($C_9H_{19}COOH$), caproic acid ($C_5H_{11}COOH$), oleic acid ($C_{17}H_{33}COOH$), caprylic acid ($C_7H_{15}COOH$), erucic acid ($C_{21}H_{41}COOH$), butyric acid ($C_3H_7COOH$), ethyl myristate ($C_{13}H_{27}COOC_2H_5$), ethyl oleate ($C_{17}H_{33}COOC_2H_5$), ethyl palmitate ($C_{15}H_{31}COOC_2H_5$), ethyl linoleate ($C_{17}H_{31}COOC_2H_5$), ethyl laurate ($C_{11}H_{23}COOC_2H_5$), ethyl linolenate ($C_{17}H_{29}COOC_2H_5$), ethyl stearate ($C_{17}H_{35}COOC_2H_5$), ethyl arachidate ($C_{19}H_{39}COOC_2H_5$), ethyl caprilate ($C_7H_{15}COOC_2H_5$), ethyl caprate ($C_9H_{19}COOC_2H_5$), ethyl caproate ($C_5H_{11}COOC_2H_5$), ethyl butyrate ($C_3H_7COOC_2H_5$), triacetin ($C_9H_{14}O_6$), alpha tocopherol ($C_{29}H_{50}O_2$), beta tocopherol ($C_{28}H_{48}O_2$), delta tocopherol ($C_{27}H_{46}O_2$), gamma tocopherol ($C_{28}H_{48}O_2$), benzyl alcohol ($C_7H_8O$), benzyl benzoate ($C_{14}H_{12}O_2$), methylphenol ($C_7H_8O$), di-n-butyl sebacate ($C_{18}H_{34}O_4$), diethylphthalate ($C_{12}H_{14}O_4$), glyceryl monooleate ($C_{21}H_{40}O_4$), lecithin, triglycerides, mineral oil, petrolatum, and liquid paraffines.

61. The composition according to claim 37, wherein the hydrophobic liquid is a vegetable oil selected from the group consisting of:
canola oil, corn oil, cottonseed oil, peanut oil, sesame oil, castor oil, and soybean oil.

62. The composition according to claim 37, wherein said first component comprises calcium sulphate hemihydrate [$CaSO_4$-½$H_2O$], calcium pyrophosphate [$Ca_2P_2O_7$], calcium carbonate [$CaCO_3$], monocalcium phosphate monohydrate [$Ca(H_2PO_4)_2 \cdot H_2O$], monocalcium phosphate [$Ca(H_2PO_4)_2$], anhydrous dicalcium phosphate [$CaHPO_4$], dicalcium phosphate dihydrate [$CaHPO_4 \cdot 2H_2O$], octocalcium phosphate [$Ca_8H_2(PO_4)_6 \cdot 5H_2O$], alpha-tricalcium phosphate [alpha-$Ca_3(PO_4)_2$], beta-tricalcium phosphate [beta-$Ca_3(PO_4)_2$], hydroxyapatite [$Ca_5(PO_4)_3OH$], tetracalcium phosphate [$Ca_4(PO_4)_2O$], calcium-deficient hydroxyapatite, fluoroapatite ($Ca_5(PO_4)_3F$), amorphous calcium phosphate, oxyapatite [$Ca_{10}(PO_4)_6O$], calcium oxide and calcium hydroxide [$Ca(OH_2$] or a mixture of some or all of them.

* * * * *

UNITED STATES PATENT AND TRADEMARK OFFICE
CERTIFICATE OF CORRECTION

PATENT NO. : 6,642,285 B1
DATED : October 16, 2003
INVENTOR(S) : Marc Bohner

It is certified that error appears in the above-identified patent and that said Letters Patent is hereby corrected as shown below:

Column 8,
Line 65, delete "[Ca(H$_2$PO$_4$)$_2$$H$_2$O]" and replace with -- [Ca(H$_2$PO$_4$)$_2$·H$_2$O] --
Line 67, delete "[CaHPO$_4$$2H$_2$O]" and replace with -- [CaHPO$_4$·2H$_2$O] --

Column 13,
Line 3, delete "[Ca(H$_2$PO$_4$)$_2$$H$_2$O]" and replace with -- [Ca(H$_2$PO$_4$)$_2$·H$_2$O] --
Line 5, delete "[CaHPO$_4$$2H$_2$O]" and replace with -- [CaHPO$_4$·2H$_2$O] --
Line 6, delete "[Ca$_8$H$_2$(PO$_4$)$_6$$5H$_2$O]" and replace with -- [Ca$_8$H$_2$(PO$_4$)$_6$·5H$_2$O] --

Column 14,
Line 25, delete "[Ca(H$_2$PO$_4$)$_2$$H$_2$O]" and replace with -- [Ca(H$_2$PO$_4$)$_2$·H$_2$O] --
Line 27, delete "[CaHPO$_4$$2H$_2$O]" and replace with -- [CaHPO$_4$·2H$_2$O] --
Line 28, delete "[Ca$_8$H$_2$(PO$_4$)$_6$$5H$_2$O]" and replace with -- [Ca$_8$H$_2$(PO$_4$)$_6$·5H$_2$O] --

Column 15,
Line 47, delete "[Ca(H$_2$PO$_4$)$_2$$H$_2$O]" and replace with -- [Ca(H$_2$PO$_4$)$_2$·H$_2$O] --
Line 49, delete "[CaHPO$_4$$2H$_2$O]" and replace with -- [CaHPO$_4$·2H$_2$O] --
Line 50, delete "[Ca$_8$H$_2$(PO$_4$)$_6$$5H$_2$O]" and replace with -- [Ca$_8$H$_2$(PO$_4$)$_6$·5H$_2$O] --

Signed and Sealed this

Twelfth Day of October, 2004

JON W. DUDAS
*Director of the United States Patent and Trademark Office*